United States Patent
McNally et al.

(10) Patent No.: US 10,722,472 B2
(45) Date of Patent: Jul. 28, 2020

(54) SOLID SIMETHICONE PARTICLES AND DOSAGE FORM THEREOF

(71) Applicant: Johnson & Johnson Consumer Inc., Skillman, NJ (US)

(72) Inventors: Gerard P. McNally, Derwyn, PA (US); Christopher Szymczak, Marlton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/131,232

(22) Filed: Sep. 14, 2018

(65) Prior Publication Data
US 2019/0099379 A1    Apr. 4, 2019

Related U.S. Application Data

(60) Provisional application No. 62/565,850, filed on Sep. 29, 2017.

(51) Int. Cl.
| | |
|---|---|
| *A61K 9/50* | (2006.01) |
| *A61K 9/00* | (2006.01) |
| *A61K 9/20* | (2006.01) |
| *A61K 9/48* | (2006.01) |
| *A61K 31/80* | (2006.01) |

(52) U.S. Cl.
CPC .......... *A61K 9/5057* (2013.01); *A61K 9/0056* (2013.01); *A61K 9/2081* (2013.01); *A61K 9/485* (2013.01); *A61K 9/4858* (2013.01); *A61K 9/4866* (2013.01); *A61K 9/501* (2013.01); *A61K 9/5042* (2013.01); *A61K 9/5052* (2013.01); *A61K 9/5089* (2013.01); *A61K 31/80* (2013.01)

(58) Field of Classification Search
None
See application file for complete search history.

(56) References Cited

U.S. PATENT DOCUMENTS

| | | | |
|---|---|---|---|
| 5,599,577 A | 2/1997 | Stevens et al. | |
| 5,679,376 A | 10/1997 | Stevens et al. | |
| 5,716,641 A | 2/1998 | Stevens et al. | |
| 5,980,944 A | 11/1999 | Stevens et al. | |
| 6,100,245 A | 8/2000 | Sox | |
| 6,103,260 A | 8/2000 | Luber et al. | |
| 7,101,573 B2 | 9/2006 | Szymczak et al. | |
| 7,691,409 B2 | 4/2010 | Szymczak et al. | |
| 2003/0007962 A1 | 1/2003 | Vergez et al. | |
| 2009/0220611 A1* | 9/2009 | Dargelas | A61K 9/2077 424/495 |
| 2012/0207825 A1* | 8/2012 | Roy | A61K 9/2886 424/452 |

FOREIGN PATENT DOCUMENTS

| | | | | |
|---|---|---|---|---|
| EP | 1086701 A2 | 3/2001 | | |
| EP | 2085079 A | 8/2009 | | |
| EP | 2085079 A2 * | 8/2009 | ........... | A61K 9/0095 |

OTHER PUBLICATIONS

Leiberman et al., Pharmaceutical Dosage Forms—Tablets, vol. 2, 2 sup nd ed., Marcel Dekker Inc., 1990, pp. 213-217 and 327-329.

Xiao et al., "A Review of the Preparation and Application of Flavour and Essential Oils Microcapsules based on Complex Coaceration Technology", Journal of the Science of Food and Agriculture, Dec. 27, 2013, 94(8):1482-1494.

International search report and written opinion dated Dec. 12, 2018, for international application PCT/IB2018/057057.

* cited by examiner

*Primary Examiner* — Brian Gulledge

(57) ABSTRACT

The present invention is directed to microencapsulated simethicone particles containing simethicone and a water soluble coating, wherein the simethicone is about 50% by weight of the particle.

22 Claims, No Drawings

SOLID SIMETHICONE PARTICLES AND DOSAGE FORM THEREOF

CROSS-REFERENCE TO RELATED APPLICATIONS

This application claims the benefit of U.S. provisional application 62/565850 filed on Sep. 29, 2017, the complete disclosure of which is hereby incorporated herein by reference for all purposes.

BACKGROUND OF THE INVENTION

Field of the Invention

The present invention relates to novel solid simethicone particles and methods for making such particles.

Simethicone has been used to treat intestinal discomfort, pressure, fullness, and bloating. It is typically administered in a liquid or solid form either alone or in combination with antacids or anti-diarrheals, such as loperamide.

Typically, to incorporate simethicone into a solid formulation, it must first be adsorbed onto a suitable carrier or substrate. There have been several inventions related to this problem, substrate materials vary from polysaccharides to inorganic materials such as calcium phosphates or metalosilicates. A limitation of the polysaccharide approach is that the limited loading capacity i.e. a stable concentration of simethicone adsorbed onto the substrate resides in the range of 20-25% which implies a simethicone/adsorbate dose of 500-625 mg for a 125 mg dose of simethicone. A drawback of the inorganic substrates is their insolubility and gritty mouthfeel. Thus these approaches to generating solid phase simethicone powder or granules are not suitable for certain delivery formats such as orally disintegrating tablets (ODTs) or orally dispersible granules (ODGs). A microencapsulated simethicone particle with a water soluble coating would address the limitations of the existing approaches to producing free flowing simethicone powders.

The primary benefit of the novel microencapsulated simethicone particle with a water soluble coating are that it addresses the limitations of the existing approaches to producing free flowing simethicone powders. Additional benefits of the coating includes adding a separating layer between simethicone and other materials, such as active ingredients. However it may not survive a typical tablet compression process as it is likely that the microencapsulated oil particles would be ruptured. Certain ODT manufacturing processes such as sintering, freeze drying and 3D printing do not expose the ODT ingredients to excessive pressures so could enable a novel solution to making a fast dissolving simethicone containing ODT. Similarly ODG formulations would be enabled by this approach.

SUMMARY OF THE INVENTION

The present invention is directed to microencapsulated simethicone particles comprising:
simethicone and a water soluble coating, wherein the simethicone is about 50% by weight of the particle.

In one embodiment, the present invention is directed to a method of preparing microencapsulated simethicone particles comprising the steps of (a) forming a water coating solution, (b) combining simethicone and the water soluble coating solution and forming an emulsion, and (c) spray drying the emulsion.

The present invention also includes a method of preparing microencapsulated simethicone particles comprising the steps of (a) preparing simethicone granules; (b) preparing a coating solution; and (c) coating the simethicone granules with the coating solution.

The present invention also includes a method of preparing microencapsulated simethicone particles comprising the steps of (a) forming a complex coacervate of simethicone particles and hydrocolloids; (b) cooling the complex coacervate to a gel temperature at a pH of about 5 to deposit a protein shell around each of the simethicone particles; (c) further cooling the complex coacervate to a cross-linking temperature below the gel temperature at a pH of about 7 to stabilize the protein shell; and (d) adding an enzyme to the water for enzymatically cross-linking the stabilized protein shell at about pH 7 to form microencapsulated simethicone particles.

DETAILED DESCRIPTION OF THE INVENTION

The present invention is directed to a microencapsulated simethicone particle containing simethicone and a water soluble coating, wherein the simethicone is about 50% by weight of the particle.

Simethicone may be orally ingested and is typically used to relieve symptoms of excess gas such as belching, bloating and pressure in the stomach and/or intestines. It works by breaking up gas bubbles.

The simethicone particle is at least about 50% by weight simethicone. In one embodiment, the simethicone particle is from about 50% to about 99% by weight simethicone. In another embodiment, the simethicone particle is from about 60% to about 97% by weight simethicone. In still another embodiment, from about 70% to about 95% by weight of the particle.

Another essential component is a water soluble coating. Suitable water soluble coatings include, for example, gelatin, pectin, water soluble materials, combinations of water soluble materials with water insoluble materials, whey protein isolate, or mixtures thereof.

Suitable gelatins include but are not limited to Croda SPA® (45-85 Bloom), derived from specially tanned cow hides, or Type A or Type B derived from bovine skin, bovine bone, pork skin, fish. The gelatins are present at levels of 10 to 60%, more preferably 20 to 50%, most preferably 20 to 35% by weight.

In certain embodiments the coating may be partially water soluble or pH sensitive, such that it does not dissolve in the oral cavity but is immediately released in the stomach or intestine. For example, the coating may incorporate a portion of water insoluble material such as a water insoluble polymer. Suitable water insoluble polymers include but are not limited to ethylcellulose, cellulose acetate, and polymethacrylates. Suitable pH dependent polymers include cellulose acetate phthalate, hydrocypropylcellulose phthalate, shellac, hydroxypropylcellulose succinate, anionic copolymers based on methacrylic acid and methyl methacrylate such as those sold under the tradename of Eudragit L100.

In one embodiment, non-hydrolyzed gelatins are preferred.

In another embodiment, whey protein isolate containing about 98% protein is utilized as the water soluble coating.

Alternatively, the simethicone is adsorbed on anhydrous dibasic calcium phosphate and further coated with a water soluble coating.

In another embodiment, the water soluble coating may comprise a swellable erodible hydrophilic material, and a pH dependent polymer.

Examples of swellable, erodible hydrophilic materials for use in the coating include water swellable cellulose derivatives, polyalkylene glycols, thermoplastic polyalkylene oxides, acrylic polymers, hydrocolloids, clays, and gelling starches. Examples of water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose. Examples of polyalkylene glycols include polyethylene glycol. Examples of water soluble vinyl based polymers include polyvinyl alcohol, polyvinyl alcohol:polyethylene glycol copolymers and mixtures thereof. Examples of suitable thermoplastic polyalkylene oxides include poly (ethylene oxide). Examples of acrylic polymers include potassium methacrylatedivinylbenzene copolymer, polymethylmethacrylate, and high-molecular weight cross-linked acrylic acid homopolymers and copolymers.

Suitable pH-dependent polymers for use as for use in the coating include: enteric cellulose derivatives such as hydroxypropyl methylcellulose phthalate, hydroxypropyl methylcellulose acetate succinate, and cellulose acetate phthalate; natural resins such as shellac and zein; enteric acetate derivatives such as polyvinylacetate phthalate, cellulose acetate phthalate, and acetaldehyde dimethylcellulose acetate; and enteric acrylate derivatives such as for example polymethacrylate-based polymers such as poly(methacrylic acid, methyl methacrylate) 1:2 (available from Rohm Pharma GmbH under the tradename EUDRAGIT S) and poly(methacrylic acid, methyl methacrylate) 1:1 (available from Rohm Pharma GmbH under the tradename EUDRAGIT L).

In another embodiment, the coating may include a plasticizer or a surfactant. Suitable plasticizers include for example, glycerin, polyethylene glycol, propylene glycol, dibutyl sebecate, triethyl citrate, vegetable oils such as castor oil. Suitable surfactants include Polysorbate-80, sodium lauryl sulfate and dioctyl-sodium sulfosuccinate. The plasticizer may comprise from 1 percent to 30 percent by weight of the coating. The surfactant may comprise from 1 to 20 percent of the coating.

The inventive simethicone particles may be prepared using various known processing methods. For example, spray drying, fluid bed coating, or coacervation processing techniques may be utilized to form the simethicone particles.

The microencapsulated simethicone particles may be used in various applications. For example, the inventive particles may be included in an oral dosage form, such as an orally disintegrating tablet, a capsule, a compressed tablet such as a chewable tablet a lozenge, a chewing gum or a gummy form. Alternatively, the particles may be included in orally dissolving granules.

In one embodiment, the tablet is containing the encapsulated simethicone is prepared such that the tablet is relatively soft (e.g., capable of disintegrating in the mouth or being chewed). In one embodiment, the hardness of the tablet is preferably less than about 3 kiloponds per square centimeter ($kp/cm^2$) (e.g., less than about 2 $kp/cm^2$, such as less than about 1 $kp/cm^2$). Hardness is a term used in the art to describe the diametral breaking strength as measured by conventional pharmaceutical hardness testing equipment, such as a Schleuniger Hardness Tester. In order to compare values across different size tablets, the breaking strength must be normalized for the area of the break. This normalized value, expressed in $kp/cm^2$, is sometimes referred in the art as tablet tensile strength. A general discussion of tablet hardness testing is found in Leiberman et al., Pharmaceutical Dosage Forms—Tablets, Volume 2, 2.sup.nd ed., Marcel Dekker Inc., 1990, pp. 213-217, 327-329.

A more preferred test for hardness of the tablet of the present invention relies upon a Texture Analyzer TA-XT2i that is fitted with a 7 millimeter diameter flat faced probe and setup to measure and report compression force in grams. The probe moves at 0.05 millimeters per second to a depth of penetration of 2 millimeters. The maximum compression force is recorded. In one embodiment, the measured forces recorded for tablets made in accordance with the present invention are less than 10,000 grams (e.g., less than about 1000 grams, such s led than about 700 grams. In one embodiment, the measured forces recorded for tablets made in accordance with the present invention ranges from about 100 grams to about 6000 grams, such as from about 100 grams to about 1000 grams, such as from about 75 grams to about 700 grams) with a deviation of ±50 grams. In another embodiment the measured forces recorded for tablets is less than 700 grams.

Optionally, other ingredients may be included in the composition or dosage form of the present invention.

The microencapsulated simethicone particles may be combined with any active pharmaceutical ingredient ("API").

For example, the API may be for, analgesics, anti-inflammatories, antipyretics, antihistamines, decongestants, cough suppressants and expectorants, muscle relaxants, stimulants, sedatives, appetite suppressants, anesthetics, statins, antidiarrheal agents, H2 antagonists, proton pump inhibitors, antacids and the like. More specifically, the API may include famotidine, calcium carbonate, aluminum hydroxide, magnesium hydroxide, magnesium oxide, loperamide, and/or racecadotril.

For example, a glidant may also be included in the core composition to assist in the flow properties of the composition. Suitable glidants include, for example, silicon dioxide such as colloidal silica, fumed silica, mixtures thereof, and the like.

In one embodiment, the core may include from about 0.01 to about 3 wt. % of the glidant. In another embodiment, the core includes from about 0.05 to about 2 wt. % of the glidant. In yet another embodiment, the core includes from about 0.1 to about 1 wt. % of the glidant.

Other ingredients or components that may be added to the composition include, but are not limited to, superdisintegrants, lubricants, aromas; sweeteners such as, sorbitol, sugar, and high intensity sweeteners such as sucralose, aspartame and saccharine and the like may be included.

Any coloring agent suitable for use in a food or pharmaceutical product may be used in the present inventive composition. Typical coloring agents include, for example, azo dyes, quinopthalone dyes, triphenylmethane dyes, xanthene dyes, indigoid dyes, iron oxides, iron hydroxides, titanium dioxide, natural dyes, and mixtures thereof. More specifically, suitable colorants include, but are not limited to patent blue V, acid brilliant green BS, red 2G, azorubine, ponceau 4R, amaranth, D&C red 33, D&C red 22, D&C red 26, D&C red 28, D&C yellow 10, FD&C yellow 5, FD&C yellow 6, FD&C red 3, FD&C red 40, FD&C blue 1, FD&C blue 2, FD&C green 3, brilliant black BN, carbon black, iron oxide black, iron oxide red, iron oxide yellow, titanium dioxide, riboflavin, carotenes, antyhocyanines, turmeric, cochineal extract, clorophyllin, canthaxanthin, caramel, betanin, and mixtures thereof.

Similarly, a flavor may be included in the composition or solid dosage form. The amount of flavor added to the composition will be dependent upon the desired taste characteristics.

The microencapsulated simethicone particles are from about and average of 20 microns to about 400 microns in size. Preferably, from about 50 microns to about 200 microns in size.

The microencapsulated simethicone particles are useful in various applications, particularly in pharmaceutical and over the counter medicine products. In the present invention, the simethicone may be present in various forms prior to or upon microencapsulation or coating. The simethicone may be present as a pure oil, as an emulsion mixed with various emulsification materials, or adsorbed onto a solid substrate. Suitable emulsification materials may include but are not limited to emulsifiers such as fats, lipids; monoglycerides, diglycerides and triglycerides and mixtures thereof.

In one embodiment, the microencapsulated simethicone particles of the present invention may be compressed with other components to form a tablet or as at least one layer of a multilayer tablet. In another embodiment the microencapsulated simethicone particles may be deposited into a capsule form. In another embodiment, the microencapsulated simethicone particles may be used for direct administration from a sachet.

The microencapsulated simethicone particles may be prepared by any suitable process.

In one embodiment, the microencapsulated simethicone particles are prepared by spray drying. The process comprises the steps of (a) forming a water coating solution, (b) combining simethicone and the water soluble coating solution and forming an emulsion, and (c) spray drying the emulsion. Optionally, silicon dioxide may be added during spray drying as a flow agent. In various embodiments, the process may include the step of adjusting the pH of the water soluble coating solution to a pH of 7. Optionally, an organic solvent may also be added to the spray drying solution. Suitable organic solvents may include ethanol, isopropanol, or acetone.

In another embodiment, the microencapsulated simethicone particles are prepared by spray congealing. The process comprises the steps of (a) melting a suitable wax, lipid or combination of waxes; (b) combining the simethicone and mixing; and (c) spraying the particulates at a temperature which will solidify the particles and (d) collecting the microencapsulated particles.

The microencapsulated simethicone particles may also be made using a fluidized bed. The process comprises the steps of (a) preparing simethicone granules; (b) preparing a coating solution; and coating the simethicone granules with the coating solution.

Alternatively, the microencapsulated simethicone particles may be prepared by coacervation. In one embodiment, the complex coacervation process comprises the steps of (a) forming a complex coacervate of simethicone particles and hydrocolloids; (b) cooling the complex coacervate to a gel temperature at a pH of about 5 to deposit a protein shell around each of the simethicone particles; (c) further cooling the complex coacervate to a cross-linking temperature below the gel temperature at a pH of about 7 to stabilize the protein shell; and (d) adding an enzyme to the water for enzymatically cross-linking the stabilized protein shell at about pH 7 to form stable protein-encapsulated simethicone particles. In another embodiment, a simple or phase separation coacervation process is utilized. The simple coacervation process involves adding a first polymer (coating agent) to an organic solvent. The simethicone is then dispersed in a second organic solvent which is then added to the first organic solvent containing the polymer. The precipitate is then filtered, collected and dried as a coated particle.

The following examples are provided to further illustrate the compositions and methods of the present invention. It should be understood that the present invention is not limited to the example described.

EXAMPLE 1

Example 1

Preparation of Encapsulated Simethicone utilizing a Spray Drying Process and Gelatin

TABLE 1

| Component | Batch w/w (g) |
| --- | --- |
| Simethicone | 3000 |
| Non-Hydrolyzed Gelatin | 1500 |
| Water (removed upon drying) | 6000 |
| Syloid 74[2] | 31.5 |
| Total | 10531.5 |
| | (4531.5 g as solids) |

[2]Commercially available from W. R. Grace and Company

Part A: Procedure
1. Add water to a suitable sized (2 L) vessel and heat to 60° C.
2. Disperse gelatin into hot water while mixing, continue until dissolved.
3. Add simethicone to the solution and emulsify.
4. Spray dry solution in a Niro Utility Spray Drier.
5. Add Syloid (silicon dioxide) to the spray chamber.
6. Collect the encapsulated simethicone particles.

Example 2

Manufacture of Orally Disintegrating Tablet Containing Encapsulated Simethicone

The following tablet is prepared using the encapsulated simethicone granules from Example 1. The dose of simethicone is equivalent to 125 mg of simethicone.

Table 2 lists the components in a powder blend needed to manufacture an orally disintegrating tablet.

Sucralose, flavor, polyethylene glycol and maltodextrin from Table 2 are passed through a 20 mesh screen. The sieved materials are placed into a 500 cc plastic bottle and blended end over end with the remaining materials in Table 2.

Description of the Tablet Activation Process

A portion of the powder blend from Table 2 is placed into an electrically insulative Teflon, or ceramic die platen having a forming cavity that is approximately 1.1 inches in diameter and 0.175 inches thick. The powder blend is then tamped between upper and lower metal forming tools, into a shape conformal to the surface of the forming tools. The tamping pressure is typically between 10 and approximately 100 psi of pressure. The forming tools, die platen and tablet shape are then placed between the upper RF electrode and lower RF electrode of an RF heating unit using a COSMOS Model C10X16G4 (Cosmos Electronic Machine Corporation, Farmingdale, N.Y.) RF generator having an output of 4 KW of power and a frequency of 27 MHz). The upper RF electrode is brought into contact with the upper forming tool and the lower RF electrode is brought into contact with the lower forming tool. The RF heating unit is energized for 5 seconds. After cooling, the resulting tablet is then ejected from the die platen using the lower forming tool.

TABLE 2

Powder Blend Formulation Containing Simethicone

| Ingredient | G/Batch | Mg/Tablet |
|---|---|---|
| Dextrose Monohydrate | 246.81 | 246.81 |
| Encapsulated Simethicone (66% Potency) | 189.39 | 189.39 |
| Polyethylene Glycol 8000[1] | 51.43 | 51.43 |
| Maltodextrin[2] | 105.00 | 105.00 |
| Orange Flavor | 1.71 | 1.71 |
| Sucralose USP | 1.37 | 1.37 |
| Citric Acid USP Anhydrous | 4.29 | 4.29 |
| Total | 600.00 | 600.00 |

[1]Commercially available from Clariant PF in Rothausstr, Switzerland
[2]Commercially available from National Starch in Bridgewater, NJ Example 3

Encapsulation of Simethicone Granules by Fluid Bed Coating

Part A: Adsorbed Simethicone Granules using Anhydrous Dibasic Calcium Phosphate
1) Add 700 g of granular anhydrous dibasic calcium phosphate, (Emcompress. RTM. Anhydrous, Mendell, Paterson, N.J.) to the mixing bowl of a Kitchen Aid mixer.
2) While mixing at low speed, add 200 gm of simethicone USP over a period of 5 minutes.
3) Continue mixing at low speed for an additional 5 minutes.
4) Add 7.5 gm of silicon dioxide and mix an additional 5 minutes.
This intermediate is a free flowing granulation with no large agglomerates.
Part B: Preparation of Coating Solution and Polymer Coating of Simethicone Granules:
1) Add 1572 g of Acteone to a suitable mixing vessel (5 L stainless steel vessel)
2) While mixing slowly, add 203.6 g of Cellulose Acetate (CA298-10, 38% acetyl content) and 10.7 g of Eudragit® E-100 over 5 minutes, and mix until dissolved. The ratio of Cellulose acetate to Eudragit® E100 is 95:5. The final solution solids percentage is 12%.
3) Add 500 g of the simethicone granules from Part A to a Glatt GPGC 1/3. Coat the granules with the coating solution from Step 2, at a rate of approx. 5-8 g/minute until coated drug particles containing 10% by weight of the polymer coating are obtained.

Example 4

Manufacture of Orally Disintegrating Tablet Containing Encapsulated Simethicone (by Fluid Bed Drying)

The following tablet is prepared using the coated simethicone granules in Example 3. The dose is equivalent to 62.5 mg of simethicone.

The powder blend for an orally disintegrating tablet, containing the ingredients of Table 3, is manufactured as follows. The sucralose, flavor, polyethylene glycol and maltodextrin from the formula in Table 3 are passed through a 20 mesh screen. The sieved materials are placed into a 500 cc plastic bottle and blended end over end with the remaining materials in Table 3. The powder blend is placed into an upper and lower set of ½ inch flat faced forming tools, tamped, and activated with RF energy as described in Example 2 for approximately 2 minutes to form an orally disintegrating tablet. The resulting tablet is then removed from the die.

TABLE 3

Powder Blend Formulation Containing Simethicone

| Ingredient | G/Batch | Mg/Tablet |
|---|---|---|
| Dextrose Monohydrate | 193.25 | 193.25 |
| Encapsulated Simethicone (19.8% Potency) | 315.65 | 315.65 |
| Polyethylene Glycol 8000[1] | 60.00 | 60.00 |
| Maltodextrin[2] | 122.5 | 122.5 |
| Orange Flavor | 2.00 | 2.00 |
| Sucralose USP | 1.60 | 1.60 |
| Citric Acid USP Anhydrous | 5.00 | 5.00 |
| Total | 700.00 | 700.00 |

[1]Commercially available from Clariant PF in Rothausstr, Switzerland
[2]Commercially available from National Starch in Bridgewater, NJ Example 5

Spray Drying Preparation of Simethicone Granules using Whey Protein Isolate

TABLE 4

Materials for Simethicone Granules using Whey Protein Isolate

| Batch # | Batch w/w (g) |
|---|---|
| Simethicone | 2750 |
| Whey Protein Isolate[1] (98% protein) | 100 |
| Water (removed upon drying) | 10000 |
| Syloid 74[2] | 32.0 |
| TOTAL | 12882.0 (2882.0 g as solids upon drying) |

[1]Commercially available from Bipro Davisco Foods International
[2]Commercially available from W. R. Grace and Company Part A: Procedure for Preparing the Encapsulated Simethicone (Using the Formula in Table 4)
Simethicone Oil Emulsion and Particulate Preparation using Spray Drying
1. Add water to a suitable sized (20 L) vessel at 20° C.
2. Disperse whey protein isolate into hot water while mixing until dissolved. Adjust pH to 7.0 using 0.1 m NaOH/HCl.
3. Slowly add simethicone to the solution (over 5 minute time period) while mixing and emulsifying.
4. Homogenize the emulsion using a 2 stage homogenizer.
5. Pass the whey protein-simethicone emulsion through a plate heat exchanger held at 82° C. to facilitate cross linking.
6. Spray dry the solution in a Niro Utility Spray Drier.
7. Add the Syloid (silicon dioxide) to the spray chamber.
8. Collect the encapsulated simethicone particles.

Example 6

Manufacture of Orally Disintegrating Tablet Containing Simethicone Granules (using Whey Protein Isolate)

The following tablet is prepared using the coated simethicone granules in Example 5. The dose is equivalent to 125 mg of simethicone.

The powder blend for an orally disintegrating tablet, containing the ingredients of Table 5, is manufactured as follows. The sucralose, flavor, polyethylene glycol and maltodextrin from the formula in Table 5 are passed through a 20 mesh screen. The sieved materials are placed into a 500 cc plastic bottle and blended end over end with the remaining materials in Table 5. The powder blend is placed into an upper and lower set of ½ inch flat faced forming tools, tamped, and activated with RF energy as described in Example 2 for approximately 2 minutes to form the orally disintegrating tablet and subsequently removed from the die.

TABLE 5

Powder Blend Formulation Containing Simethicone

| Ingredient | G/Batch | Mg/Tablet |
| --- | --- | --- |
| Dextrose Monohydrate | 229.48 | 229.48 |
| Encapsulated Simethicone (~95% Potency) | 131.57 | 131.57 |
| Polyethylene Glycol 8000[1] | 42.85 | 42.85 |
| Maltodextrin[2] | 87.50 | 87.50 |
| Orange Flavor | 2.00 | 2.00 |
| Sucralose USP | 1.60 | 1.60 |
| Citric Acid USP Anhydrous | 5.00 | 5.00 |
| Total | 500.00 | 500.00 |

[1]Commercially available from Clariant PF in Rothausstr, Switzerland
[2]Commercially available from National Starch in Bridgewater, NJ

Example 7

Preparation of Simethicone Microcapsules by Coacervation

Part A: Procedure for Preparing the Simethicone Microcapsules by Coacervation
1. Add deionized water to a suitable sized (20 L) vessel and heated to 50° C.
2. Add 18.70 g of carboxymethylcellulose and 1.86 g of Gum Arabic powder while mixing until dissolved.
3. Cool the mixture from Step 2 to 35-40° C.
4. Mix 1863.1 g of Gelatin 250 bloom type A with 1678 g of deionized water until completely dissolved.
5. Cool the gelatin solution from Step 4 to 35-40° C. and add to the Gum Arabic mixture from Step 3.
6. Prepare a solution of 50 w/w sodium hydroxide in 5500 g of deionized water and heat in a suitable vessel to 35-40° C.
7. Prepare a solution of 50 w/w citric acid in 5500 g of deionized water and heat in a suitable vessel to 35-40° C.
8. Add 1491 g of simethicone to the combined Gelatin and Gum Arabic solution from Step 5 and mix until the droplets are between about 100-300 microns.
9. Adjust the pH of the solution to between 5.0 and 5.6.
10. Cool the combined solution to 25° C., at a rate of 1° C. per 5 minutes, and then cool to 10° C. and adjust to pH of 7.0 utilizing sodium hydroxide.
11. Slowly add 2.33 g of Transglutamase and agitate for 16 hours at 10° C.
12. Adjust the batch to a pH of 2.75 utilizing 50% citric acid and mix for 30 minutes.
13. Filter, remove, and try dry the capsules at 60° C. in an oven for 10 hours.

Example 8

Manufacture of Orally Disintegrating Tablet Containing Simethicone Microcapsules (by Coacervation)

The following tablet is prepared using the coated simethicone microcapsules in Example 7. The dose is equivalent to 62.5 mg of simethicone.

The powder blend for an orally disintegrating tablet, containing the ingredients of Table 6, is manufactured as follows. The sucralose, yellow colorant, flavors, polyethylene glycol and maltodextrin from the formula in Table 6 are passed through a 20 mesh screen. The sieved materials are placed into a 500 cc plastic bottle and blended end over end with the remaining materials in Table 6. The powder blend is placed into an upper and lower set of ½ inch flat faced forming tools, tamped, and activated with RF energy as described in Example 2 for approximately 2 minutes to form the orally disintegrating tablet and subsequently removed from the die.

TABLE 6

Powder Blend Formulation Containing Simethicone

| Ingredient | G/Batch | Mg/Tablet |
| --- | --- | --- |
| Dextrose Monohydrate | 294.15 | 294.15 |
| Encapsulated Simethicone (~44% Potency) | 142.05 | 142.05 |
| Polyethylene Glycol 8000[1] | 51.43 | 51.43 |
| Maltodextrin[2] | 105.00 | 105.00 |
| Orange Flavor | 1.71 | 1.71 |
| Sucralose USP | 1.37 | 1.37 |
| Citric Acid USP Anhydrous | 4.29 | 4.29 |
| Total | 600.00 | 600.00 |

[1]Commercially available from Clariant PF in Rothausstr, Switzerland
[2]Commercially available from National Starch in Bridgewater, NJ

Example 9

Manufacture of Orally Disintegrating Tablet Containing Encapsulated Simethicone and Loperamide The following tablet is also prepared using the encapsulated simethicone granules in Example 1. The dose of simethicone is equivalent to 125 mg of simethicone. The tablet also contains loperamide HCl with a dose of 2 mg.

The powder blend for an orally disintegrating tablet, containing the ingredients of Table 2, is manufactured as follows. The sucralose, flavor, polyethylene glycol, loperamide HCl and maltodextrin from the formula in Table 7 are passed through a 20 mesh screen. The sieved materials are placed into a 500 cc plastic bottle and blended end over end with the remaining materials in Table 7. The powder blend is placed into an upper and lower set of ½ inch flat faced forming tools, tamped, and activated with RF energy as described in Example 2 for approximately 2 minutes to form the orally disintegrating tablet and subsequently removed from the die.

TABLE 7

Powder Blend Formulation Containing Simethicone

| Ingredient | G/Batch | Mg/Tablet |
|---|---|---|
| Dextrose Monohydrate | 244.81 | 244.81 |
| Encapsulated Simethicone (66% Potency) | 189.39 | 189.39 |
| Polyethylene Glycol 8000[1] | 51.43 | 51.43 |
| Loperamide HCl | 2.00 | 2.00 |
| Maltodextrin[2] | 105.00 | 105.00 |
| Orange Flavor | 1.71 | 1.71 |
| Sucralose USP | 1.37 | 1.37 |
| Citric Acid USP Anhydrous | 4.29 | 4.29 |
| Total | 600.00 | 600.00 |

[1]Commercially available from Clariant PF in Rothausstr, Switzerland
[2]Commercially available from National Starch in Bridgewater, NJ

Example 10

Preparation of Simethicone Encapsulated in Isomalt

Part A: Procedure for Preparing the Simethicone Encapsulated Granules 200 g of isomalt is heated in a stainless steel vessel to approximately 166° C. to 170° C. While mixing, approximately 400 g of simethicone is dispersed into the isomalt. The molten mixture is then passed (extruded) through a 40 mesh screen and manually chopped into individual granules using a metal spatula. The resulting granules contain approximately 66.7% simethicone.

Example 11

Preparation of Encapsulated Simethicone utilizing a Spray Drying Process and Polymer (Ethylcellulose)

TABLE 8

Encapsulation Procedure using Ethylcellulose

| Batch # | Batch w/w (g) |
|---|---|
| Simethicone | 3000 |
| Ethylcellulose[a] | 1157 |
| Triethylcitrate | 129 |
| Ethanol | 17000 |
| Syloid 74[2] | 31.5 |
| Total | 21317.5 |
|  | (4317.5 g as solids) |

[2]Commercially available as Ethocel from Dow Corporation

Part A: Procedure for Preparing the Encapsulated Simethicone (using Formula from Table 8)
1. Add ethanol to a suitable sized (2 L) vessel.
2. Add ethylcellulose and triethylcitrate into the ethanol while mixing until completely dissolved.
3. Add simethicone to the solution and emulsified.
4. Spray dry the solution in a Niro Utility Spray Drier.
5. Add the Syloid (silicon dioxide) to the spray chamber.
6. Collect the encapsulated simethicone particles.

Example 12

Manufacture of Orally Disintegrating Tablet Containing Encapsulated Simethicone

The following tablet is prepared using the encapsulated simethicone granules in Example 11, utilizing the tablet process in Example 2. The dose of simethicone is equivalent to 125 mg of simethicone The powder blend for an orally disintegrating tablet, containing the ingredients of Table 9, is manufactured as follows. The sucralose, flavor, polyethylene glycol and maltodextrin from the formula in Table 2 are passed through a 20 mesh screen. The sieved materials are placed into a 500 cc plastic bottle and blended end over end with the remaining materials in Table 9. The powder blend is placed into an upper and lower set of ½ inch flat faced forming tools, tamped, and activated with radiofrequency (RF) energy using the activation process described in Example 2 for approximately 2 minutes to form the orally disintegrating tablet and subsequently removed from the die.

TABLE 9

Powder Blend Formulation Containing Simethicone

| Ingredient | G/Batch | Mg/Tablet |
|---|---|---|
| Dextrose Monohydrate | 255.94 | 255.94 |
| Encapsulated Simethicone (69.5% Potency) | 179.86 | 179.86 |
| Polyethylene Glycol 8000[1] | 51.43 | 51.43 |
| Maltodextrin[2] | 105.00 | 105.00 |
| Orange Flavor | 1.71 | 1.71 |
| Sucralose USP | 1.37 | 1.37 |
| Citric Acid USP Anhydrous | 4.29 | 4.29 |
| Total | 600.00 | 600.00 |

[1]Commercially available from Clariant PF in Rothausstr, Switzerland
[2]Commercially available from National Starch in Bridgewater, NJ

Example 13

Wettability Method for Simethicone Powders

Formula:
SIMETHICONE LV 150.0 g
NEUSILIN US2 175.0 g
STEARIC ACID 6.75 g

Neusilin powder was placed in a planetary mixer on low speed and simethicone liquid was gradually added until uniform. One gram of material was compressed on Natoli hand press to average hardness of 3.6 kp (11/16 inch round flat faced tooling) for each "slug" or tablet. Approximately 100 tablets were compressed and remaining powder blend set aside (uncoated powder for analysis). Tablets were ground into granules using a glass mortar and pestle and coated using a VFC micro fluid bed with aqueous solution containing hydroxyethyl cellulose, glycerin and sodium citrate using target parameters for inlet temperature of 70-80 C, air flow of 50-110 LPM, 12 psi spray atomization and approximately 1 g/min. Coating level was 1% by weight of each component of the coating solution.

1. A small plastic lid was inverted and used as a sample holder and overfilled with test powder and then carefully leveled to provide a continuous flat powder bed.
2. A plastic USP dropper was filled with purified water and placed vertically above surface using a clamp and ring stand.
3. A camera (Samsung SPH-L710 (S3)) with macro feature was placed level directly horizontal to the leveled surface.
4. The dropper was squeezed allowing a single drop of fixed volume (USP droplet) onto the test surface and a photo was taken.
5. The photo was analyzed using by photoshop carefully counting the pixels in the horizontal and vertical of the drop on the surface. (The height over the horizontal leg was used to calculate contact angle.)

Tan θ=(height (pixels))/(horizontal leg (pixels))

The slugged/coated material has increased wetting over the uncoated (38.6 vs 42.8), therefore indicating that the hydrophobic simethicone is less available for contact with water when coated.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

The invention claimed is:

1. Microencapsulated simethicone particles comprising: simethicone and a water soluble coating,
    wherein the simethicone is at least about 50% by weight of the particle;
    and wherein the water soluble coating is gelatin, anhydrous dibasic calcium phosphate, whey protein isolate, or mixtures thereof.

2. The particles of claim 1, wherein the gelatin is non-hydrolyzed.

3. The particles of claim 1, wherein the particle is prepared by spray drying, fluid bed coating, or coacervation.

4. The particles of claim 1, wherein the particle is from about 60% to about 97% by weight simethicone.

5. The particles of claim 1, wherein the particles are from about 50 microns to about 200 microns.

6. An orally disintegrating tablet comprising microencapsulated simethicone particles, the particles comprising simethicone and a water soluble coating, wherein the simethicone is at least about 50% by weight of the particle.

7. Orally dissolving granules comprising microencapsulated simethicone particles, the particles comprising simethicone and a water soluble coating, wherein the simethicone is at least about 50% by weight of the particle.

8. A method for making a microencapsulated simethicone particles of claim 1 comprising the steps of:
    (a) forming a water coating solution,
    (b) combining simethicone and the water soluble coating solution and forming an emulsion, and
    (c) spray drying the emulsion.

9. The method of claim 8, wherein the water soluble coating is gelatin or whey protein isolate.

10. The method according to claim 9, wherein said gelatin is unhydrolyzed.

11. The method according to claim 9, wherein said gelatin content is 20-35%.

12. The method of claim 8, further comprising the step of adjusting the pH of the water soluble coating solution to a pH of 7.

13. The method of claim 8, wherein silicon dioxide is added during spray drying.

14. An oral dosage form comprising the particles of claim 8.

15. A method of making microencapsulated simethicone particles of claim 1 comprising the steps of:
    (a) preparing simethicone granules;
    (b) preparing a coating solution; and
    (c) coating the simethicone granules with the coating solution.

16. The method of claim 15, wherein the simethicone granules preparation comprises simethicone, anhydrous dibasic calcium phosphate, and silicon dioxide.

17. The method of claim 15, wherein the coating solution comprises acetone and cellulose acetate.

18. An oral dosage form comprising the particles of claim 15.

19. A method of preparing microencapsulated simethicone particles of claim 1 comprising:
    (a) forming a complex coacervate of simethicone particles and hydrocolloids;
    (b) cooling the complex coacervate to a gel temperature at a pH of about 5 to deposit a protein shell around each of the simethicone particles;
    (c) further cooling the complex coacervate to a cross-linking temperature below the gel temperature at a pH of about 7 to stabilize the protein shell; and
    (d) adding an enzyme to the water for enzymatically cross-linking the stabilized protein shell at about pH 7 to form microencapsulated simethicone particles.

20. The method of claim 19, wherein the microencapsulated simethicone particles are from about 50 microns to about 200 microns.

21. The method of claim 19 wherein the complex coacervate is formed from an emulsion of two oppositely charged colloids.

22. An oral dosage form comprising the particles of claim 19.

* * * * *